(12) United States Patent
Korotkov

(10) Patent No.: US 7,595,868 B2
(45) Date of Patent: Sep. 29, 2009

(54) METHOD FOR DETERMINING HAIR CONDITIONS

(76) Inventor: Konstantin Georgievich Korotkov, Kuznechny per., d.14B, kv.6, Saint Petersburg (RU) 191040

( * ) Notice: Subject to any disclaimer, the term of this patent is extended or adjusted under 35 U.S.C. 154(b) by 41 days.

(21) Appl. No.: 11/814,173

(22) PCT Filed: Jun. 30, 2005

(86) PCT No.: PCT/RU2005/000370

§ 371 (c)(1),
(2), (4) Date: Feb. 8, 2008

(87) PCT Pub. No.: WO2006/078190

PCT Pub. Date: Jul. 27, 2006

(65) Prior Publication Data

US 2008/0259322 A1   Oct. 23, 2008

(30) Foreign Application Priority Data

Jan. 18, 2005   (RU)   .............................. 2005101310

(51) Int. Cl.
*G01N 21/00* (2006.01)
(52) U.S. Cl. .................................................. 356/237.1
(58) Field of Classification Search ........................ None
See application file for complete search history.

(56) References Cited

U.S. PATENT DOCUMENTS 3,863,653 A * 2/1975 Boudouris et al. .......... 132/200
4,140,902 A * 2/1979 Young ........................ 250/225
5,319,578 A * 6/1994 Lawson et al. ......... 250/559.24
7,211,083 B2 * 5/2007 Chornenky et al. ........... 606/44

* cited by examiner

Primary Examiner—Gregory J Toatley, Jr.
Assistant Examiner—Jarreas C. Underwood
(74) Attorney, Agent, or Firm—John D. Gugliotta, PE, Esq.

(57) ABSTRACT

The invention relates to cosmetology and can be used, in particular, for selecting the most suitable hair care means.

According to the inventive method for determining hair conditions, which consists in subjecting a hair strand to the influence of an electromagnetic field, which induces the glow of the hair, and subsequently measuring the intensity of the light emission radiated by hair, the hair is subjected to the influence of the electromagnetic field at its end surfaces, whereupon the intensity of the light emission radiated by the hair at its end surfaces is measured per unit area of the total area of the hair end surfaces ($I_1$), and then, along with the electromagnetic field's influence upon the end surfaces of hair, the side surface of the hair strand is subjected to the influence of an electric or electromagnetic field, whereupon the intensity of the light emission radiated by the hair at its end surfaces is again measured per unit area of the total area of the hair end surfaces ($I_2$), the $I_2 - I_1$ value is calculated and used for assessing the hair conditions.

The inventive method allows increasing the intensity of the emission from the hair influenced by the electromagnetic field, thus increasing the values of the signal/noise ratio within the measuring channel, as well as leveling the values of the excited light emission radiated by different hair samples of the same individual; furthermore, the invention allows evaluating the rate of decomposition of hair after its removal from the skin surface.

1 Claim, 3 Drawing Sheets

METHOD FOR DETERMINING HAIR CONDITIONS

TECHNICAL FIELD

The invention relates to cosmetology and can be used, in particular, for selecting the most suitable hair care means.

BACKGROUND ART

Currently a series of hair characteristics determining certain hair properties is known, which can be divided into 4 groups:

1. Morphological characteristics—size, shape, structure of the hair ends, properties of pigment and the cuticle pattern, peculiarities of the core structure and the transverse sections, presence or absence of hair injuries and diseases.
2. Biological characteristics—group and enzymatic specificity, sexual identity.
3. Characteristics of chemical properties of hair—elemental composition, changes of the hair along its length and at the cut points owing to the influence of heavy metals' salts, acids, alkalis, etc.
4. Characteristics of physical properties of hair—elasticity, refraction, specific density, transparency, electrical and other properties.

The morphological properties are the most comprehensively studied hair properties and are widely used for evaluating the hair conditions; however, the analysis of hair is most effective when a large amount of properties, including electrophysical, is thoroughly and integrally studied.

A known method for determining the hair conditions consists in studying its macroscopic properties.

The study of the hair colour. This characteristic is of particular importance during forensic medical examination of hair and depends on the amount and colour of pigment contained in the hair and on the nature of the cuticle: the smoother the cuticle, the greater the dispersion of light is and the lighter the hair looks. The presence of air bubbles in the hair also makes them look lighter. However, the hair colour also depends on the personal perception of the observer, which makes the study of hair a difficult task even for a single observer.

According to Broca's classification, there are 54 shades of the hair colour. A. K. Tumanov defines the colour of a hair strand as one of the following: blond, light brown, brown, dark brown, black, grey, red (see A. K. Tumanov. Foundations of the forensic medical examination. M., 1976, p. 308-382). G. G. Avtandilov recommends using a seven-step scale: light-blond, blond, dark-blond, light-brown, brown, black. The colour of a single hair is defined as white, yellow, light-brown, brown, dark-brown or black; however, the hair can have some other colour hue due to artificial dyeing, the effects of temperature and decomposition (see G. G. Avtandilov. Morphometry and pathology. M., 1976, p, 1-246).

Various physical methods for analyzing the hair conditions are known.

Determination of the Tear Strength and Elasticity of Hair

The elasticity of a hair sample depends on the thickness of the cortical layer, external influences and pathological conditions. The strength and elasticity of hair can be measured by means of a hydraulic dynamometer equipped with a self-recording device, which allows obtaining a diagram of the tearing process of the hair sample (see A. N. Kishinevsky. On the medico-legal importance of objective microphotometry of human hair. Proceedings of the 4th All-Union conference of forensic physicians Riga, 1962, p. 400-401). During the tearing process the stretching of the hair is non-uniform: at first it grows in proportion to the load and then sharply increases until a particular level of the load is reached, whereas the subsequent elongation of the hair sample, which takes place until the tearing moment, is minor. The tear diagrams for hair of different individuals have different patterns and size, and depend on the region of the hair's origin. For example, during the tearing of underarm hair the phase of the second elongation is not observed.

Average strength of hair from heads of various individuals ranges between 14 and 157 g., of underarm hair—from 35 to 132, of pubic hair—from 95 to 200 g. The elongation of hair by the moment of tearing for various individuals amounts to an average of 34% for hair from the head, 25% for underarm hair and 24% for pubic hair. The difference between the strength of hair from the head of the same individual generally does not exceed 15-25 g. and rarely reaches 40 g.; the elongation of the hair sample does not exceed 10-15% (about 1 mm). The difference in hair strength of 40 g. or the elongation of 1.5 mm indicate that the hair belongs to different individuals.

Determination of the submersion rate. This method consists in measuring the time of submersion of hair segments at a standard depth (10 cm.) into a cylinder filled with distilled water. The hair samples should be positioned strictly horizontally and should be of about the same thickness and structure (the presence of a core). For different individuals the average submersion time varies from $24.6 \pm 0.7$ to $58.8 \pm 1.8$ sec. (with amplitude of 34.2 sec.); for hair from different regions of head of the same individual the value varies from $41.9 \pm 1.3$ to $44.1 \pm 1.3$ sec. (with amplitude of 3.2 sec.), rarely reaching 16 sec. The correlation dependence between the thickness of hair and the rate of its submersion is negative and equals $0.77 \pm 0.07$ sec. (t=2). Grey hair sink more slowly ($44.6 \pm 1.3$ sec.). The colour of hair does not influence the rate of submersion (see A. N. Kishinevsky. On the medico-legal importance of objective microphotometry of human hair. Proceedings of the 4th All-Union conference of forensic physicians Riga, 1962, p. 402-403).

Several photometric methods for studying the hair conditions are known as well.

Microphotometry. The microphotometry method is based on the objective registration of the extent of light transmission by different regions of a hair sample. The optical property of hair studied in this method should be regarded only as a relative notion, because a hair constitutes an extremely complex system, which has no regular configuration and causes numerous refractions, reflections and dispersions of the light beam as it passes through the hair sample; the microphotometry of hair from the head and the regional areas is conducted with the lighting and measuring slots being 0.3 mm. wide; each hair sample is measured at 10 points with an interval of 2 mm.; the deviations of the light transmission value along the length of the hair sample are minor; the fluctuation value of the average light transmission coefficient of hair taken from different head regions of the same individual does not exceed 4%, while the same value for the hair taken from heads of different individuals varies from $5.9 \pm 0.4\%$ to $14 \pm 1.4\%$ (see L. E. Kuznetsov. The medico-legal study of damp mineralizates of human hair (comprehensive spectrophotometric, photoelectrocolorimetric and microphotometric research). Author's abstract of Ph.D. thesis, Barnaul, 1973, p. 1-23).

Photometric Study of Damp Mineralizates of Hair

This method is based on the coloured solutions' ability to absorb light waves. A ray of light passing through the solution is partly absorbed, which is registered by a number of devices: photoelectrocolorimeters, microphotometers and spectrophotometers. The values of the optical density of damp mineralizates of hair from various regions of head of the same individual were found to vary, although the difference between them is statistically unreliable. For hair of different people the difference between said values is more than twice as big as the maximum difference between the optical density values of hair of the same individual (see A. N. Kishinevsky, L. E. Kuznetsov, V. G. Kaukal. Photometry of human hair within the visible and ultraviolet spectra. Theory and practice of forensic medicine. Kazan, 1973, p. 200-203).

Another known method for determining the hair conditions consists in measuring its specific electrical resistance (see M. Z. Mamedov. Specific electrical resistance of hair during its similarity examination. Sud.med.expert, 1986, No. 4, p. 45-47).

Said method consists in measuring the overall electrical resistance, voltage and intensity of the current that flows through hair that has been degreased, washed and dried. In order to measure the overall hair resistance $R_o$, each hair region is provided with ohmic contacts made from gallium-indium eutectic (1:1). The intensity of the current is measured by means of an electrometric amplifier BK 2-16. The method is based on the principle of determining weak electric current values by measuring the value of the voltage drop.

Specific electrical resistance of hair can serve as an independent objective property, which can be used as a basis for a forensic medical examination of hair similarity; this value varies from $10^4$ to $10^{10}$ Ohm·m for different individuals, and varies with a variation coefficient between 3 and 39% for hair from different regions of head of the same individual. A statistically significant difference was found to exist between the specific electrical resistance of pigmented and grey hair, and of thin and thick hair.

The specific electrical resistance of hair does not correlate with the age of the individual and is not connected with his/her sexual dimorphism and hair colour; however, it certainly depends on the region of the hair's origin.

The methods examined above are effective mainly when used during hair similarity expertise, since they virtually exclude the possibility of a false positive conclusion for hair belonging to another individual, even when the group specificity is the same and the morphologic structure is similar.

However, the abovementioned methods provide little information on the conditions and quality of hair.

A known method of assessing the hair conditions by the quantitative characteristics of the hair properties includes the measurement of certain informative parameter of the hair sample and subsequent determination of the quantitative characteristic of the hair properties with the help of the measured parameter; the hair conditions are assessed by measuring the degree of its swelling in the water, where a hair sample of at least 18 mm. is used for the measurements, the thickness of a dry hair sample is measured and then, after the maximum water saturation of the hair sample, the degree of the hair sample swelling in water is measured by using the previously obtained thickness value, where the swelling degree S is calculated in accordance with the following formula:

$$S = \frac{S_S - S_{initial}}{S_{initial}} \times 100\%,$$

RU 2128837 C1.

The disadvantage of said method consists in that the properties of hair suffer drastic changes under the influence of water, because it acts both as a chemical agent and as a physical influence, and causes the swelling of the hair sample and subsequent destruction of its structure.

A known method for determining hair conditions consists in influencing a hair sample in transverse direction by an electromagnetic field within the range of 100 to 750 nm.; this excites the glow of the hair; then the intensity of the light emission radiated from the hair surface is measured and the obtained values are used for determining the hair conditions, DE, A1, 19506677.

This engineering solution is taken as a prototype of the present invention.

The disadvantage of the prototype consists in that the light emission of hair excited by the electromagnetic field ranging from 100 to 750 nm. (the light range) has insufficient intensity, which accounts for minor values of the signal/noise ratio within the measuring channel and subsequent low accuracy and reliability of the measurements. Besides, since the prototype method uses transversal irradiation of hair by means of the electromagnetic field, the non-uniformity of surface of different hair samples taken from the head of the same individual causes a substantial dispersion of values of the light emission radiated by different hair samples; in the long run this can produce a significant measurement error and, therefore, an incorrect assessment of the hair conditions.

Furthermore, the prototype method does not allow evaluating the rate of decomposition of hair after its removal from the skin surface.

SUMMARY OF THE INVENTION

It is an object of this invention to provide a solution for increasing the intensity of the emission of hair influenced by the electromagnetic field, thus increasing the values of the signal/noise ratio within the measuring channel, as well as leveling the values of the excited light emission radiated by different hair samples of the same individual; furthermore, the invention allows evaluating the rate of decomposition of hair after its removal from the skin surface.

According to the inventive method for determining hair conditions, which consists in subjecting a hair strand to the influence of an electromagnetic field, which induces the glow of the hair, and subsequently measuring the intensity of the light emission radiated by hair, the hair is subjected to the influence of the electromagnetic field at its end surfaces, whereupon the intensity of the light emission radiated by the hair at its end surfaces is measured per unit area of the total area of the hair end surfaces ($I_1$), and then, along with the electromagnetic field's influence upon the end surfaces of hair, the side surface of the hair strand is subjected to the influence of an electric or electromagnetic field, whereupon the intensity of the light emission radiated by the hair at its end surfaces is again measured per unit area of the total area of the hair end surfaces ($I_2$), the $I_2-I_1$ value is calculated and used for assessing the hair conditions.

The applicant hasn't found any source of information containing data on engineering solutions identical to the present invention. In applicant's opinion, this enables to conclude that the invention conforms to the criterion "Novelty" (N).

The novel features of the present invention provide a sharp increase in the intensity of the excited light emission, as well as the leveling of the values of said parameter measured for different hair samples of the same individual; also, a means for evaluating the degree of decomposition of a hair sample after its removal from the skin surface is provided for the first time.

The applicant hasn't found any source of information containing data on the influence of the inventive novel features on the technical result produced through the realization of said features. In applicant's opinion, this enables to conclude that the present engineering solution conforms to the criterion "Inventive Step" (IS).

BRIEF DESCRIPTION OF THE DRAWINGS

This invention is further explained, by way of example, with reference to the accompanying drawings, in which.

PREFERRED EMBODIMENT

Figure 1:
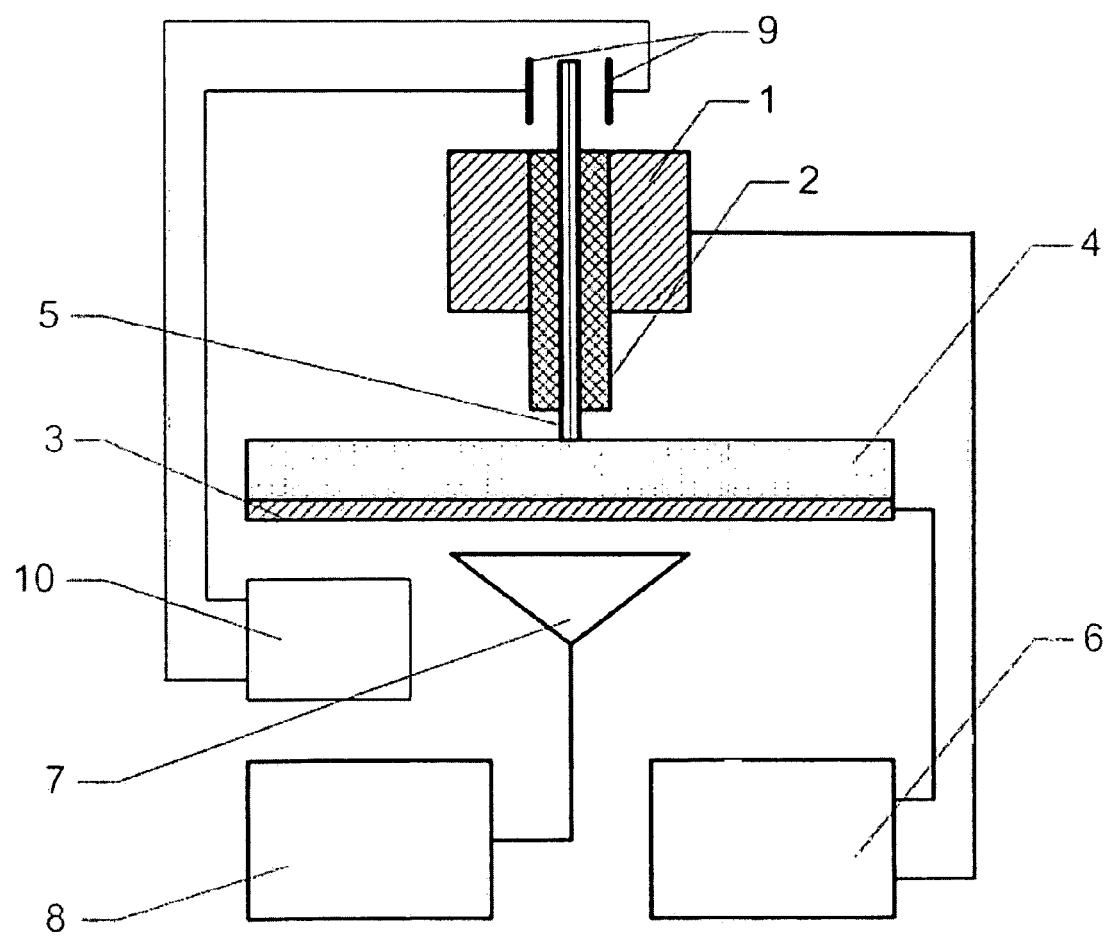
FIG. 1 is the device for realization of the inventive method.
Figure 2:
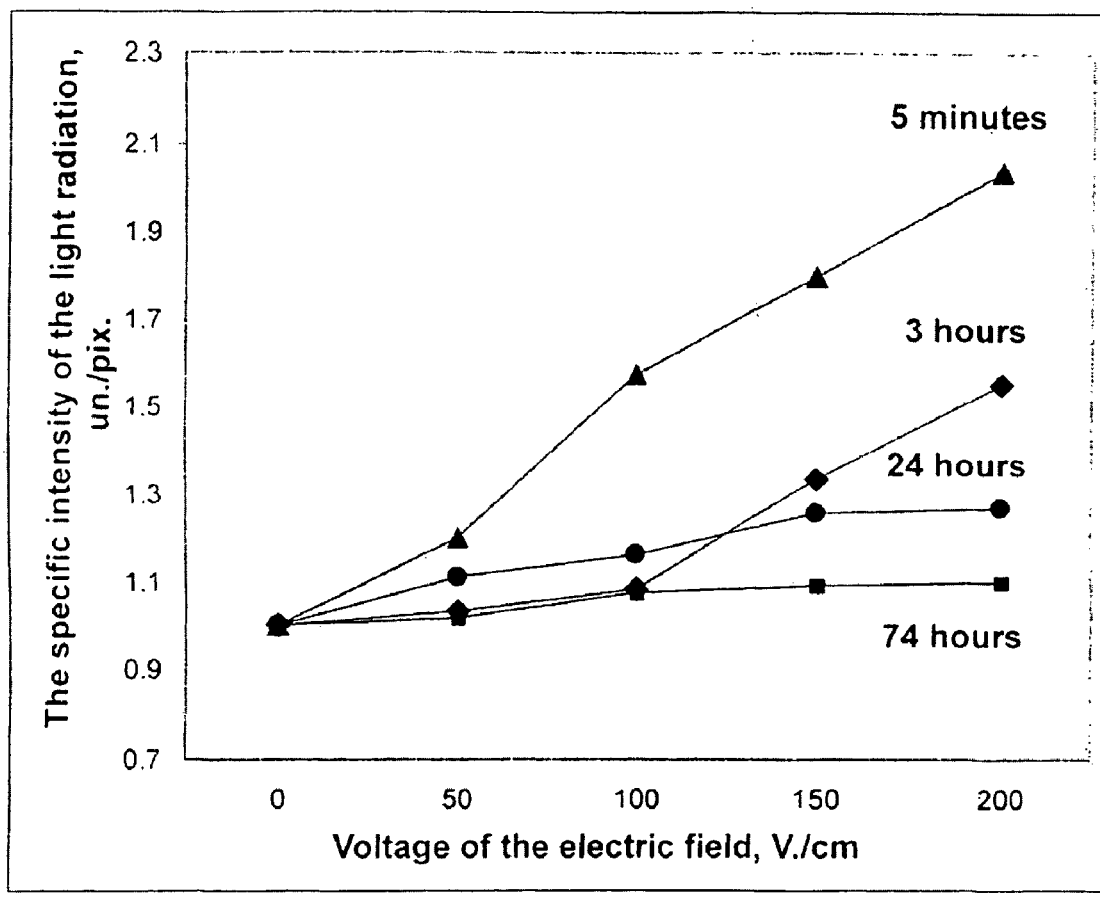
FIG. 2 is a graph of the relative intensity of the light emission radiated by the hair plotted against the voltage of the electric field influencing the side surface of the hair strand at different time points after the hair removal from the skin surface.
Figure 3:
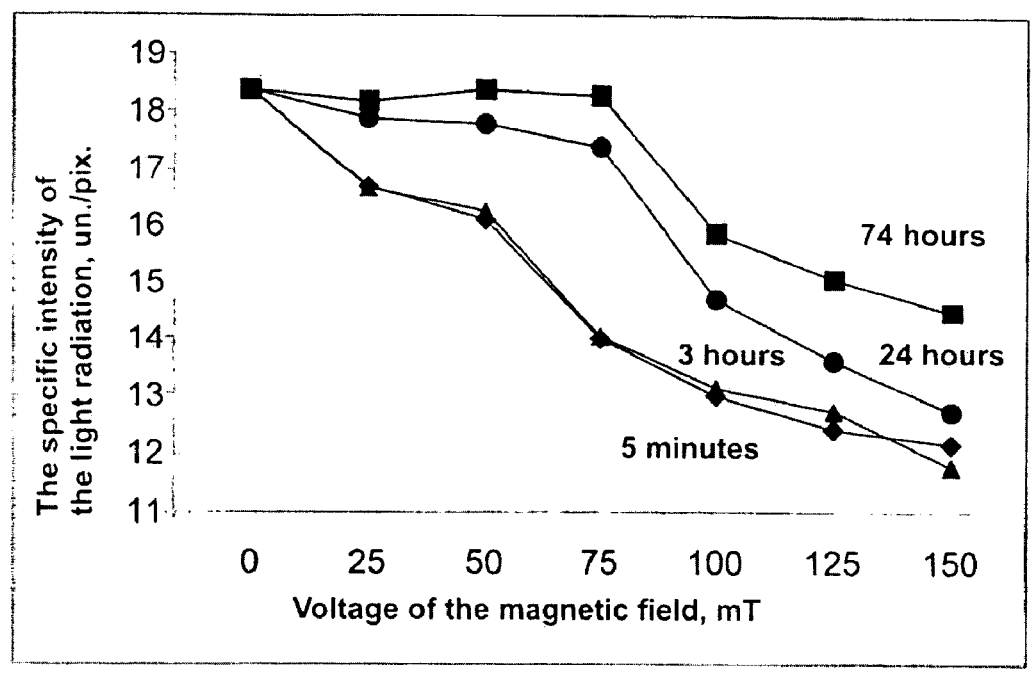
FIG. 3 is the same as FIG. 2, but for magnetic field.

The device comprises an electromagnetic field radiator, embodied as a set of two electrodes, wherein one electrode is the hair holder 1; a layer 2 of some dielectric material is placed between the hair and the hair holder 1; the second electrode is embodied in the form of an optically transparent conductive layer 3 that is applied upon one side of a plate 4 made of some optically transparent material, in particular, of glass. The other side of the plate 3 is facing the end surfaces of the hair strand 5. The electrodes are connected with the electromagnetic energy generator 6. This particular embodiment uses the electric pulse generator "Corona" manufactured by a Russian Close Joint-Stock company "Kirlionics Technologies International" (St. Petersburg). The generator provides the generation of electric pulses with amplitude of 10-20 kV, duration of 10 μsec. and off-duty factor of 1,000 Hz, wherein the pulses are served in 0.5 sec. bursts.

A receiver 7 of the light emission is connected with a device 8 for measuring the intensity of the light emission, said device in this particular embodiment being the electric block described in "From Kirlian effect to bioelectrography"/Under the editorship of K. G. Korotkov. SPb, 1998, p. 238-240.

The electric or electromagnetic field that influences the side surface of hair is generated between the electrodes 9, which are connected with a voltage source 10 (100 V.). When the electric field is used, the electrodes 9 are embodied in the form of plates, and the source 10 generates direct current (DC) voltage. When the electromagnetic field is used, the electrodes 9 are embodied in the form of inductors, and the source 10 generates alternating current (AC) voltage.

A hair strand 5 is inserted into the hair holder 1 in such a way that the end surfaces (the ends) of the hair contact with the free surface of the plate 4. Generator 6 supplies electromagnetic pulses with the wave length ranging from $10^{-2}$ m. πo $3 \times 10^{8}$ m. and the electromagnetic field intensity of $10^{4}$-$10^{6}$ V./cm._{0} to the electrodes (the hair holder 1 and the conductive layer 3), whereupon the hair is influenced at its end surfaces. The electromagnetic energy flow produces the gas discharge glow radiating from the end surfaces of the hair 5. The emitted light flow passes through the transparent plate 4, the optically transparent layer and then gets to the receiver 7 of the light emission. The signal that emerges from the output of the receiver 7 enters the measuring device 8 whereupon the intensity $I_1$ of the light emission is measured.

Then, along with the electromagnetic field's influence upon the end surfaces of hair, the side surface of the hair strand is subjected to the influence of the electric or electromagnetic field that is generated between the electrodes 9.

Then the intensity of the light emission radiated by the hair at its end surfaces is again measured per unit area of the total area of the hair end surfaces ($I_2$); then the $I_2-I_1$ value is calculated and used for assessing the hair conditions. The following table contains the $I_2-I_1$ values for hair of the same individual measured at different time points after the hair removal from the skin surface of the head.

TABLE 1

| Time elapsed after the hair removal from the skin surface | $I_2 - I_1$ value for electric field E = 150 V./cm. | $I_2 - I_1$ value for magnetic field H = mT, |
|---|---|---|
| 5 minutes | 1.80 | −6.6 |
| 3 hours | 1.33 | −6.2 |
| 24 hours | 1.25 | −5.7 |
| 74 hours | 1.09 | −3.9 |

It is obvious from the table that as the hair gradually becomes degraded after its removal from the skin surface, the absolute values of $I_2-I_1$ become smaller. Therefore, the value of $I_2-I_1$ can be used for evaluating the degree of the hair degradation. These results can be used in cosmetology, medicine and forensic medical examinations.

INDUSTRIAL APPLICABILITY

The inventive method is realized by means of well-known non-easy-to-obtain materials. Known simple industrial equipment is used for the realization of the invention, which, in applicant's opinion, enables to conclude that the invention conforms to the criterion "Industrial Applicability" (IA).

The invention claimed is:

1. A method for determining hair conditions, comprising the subjection of a hair strand to the influence of an electromagnetic field, which induces the glow of the hair, and subsequent measurement of the intensity of the light emission radiated by hair, characterized in that the hair is subjected to the influence of the electromagnetic field at its end surfaces, whereupon the intensity of the light emission radiated by the hair at its end surfaces is measured per unit area of the total area of the hair end surfaces ($I_1$), and then, along with the electromagnetic field's influence upon the end surfaces of hair, the side surface of the hair strand is subjected to the influence of an electric or electromagnetic field, whereupon the intensity of the light emission radiated by the hair at its end surfaces is again measured per unit area of the total area of the hair end surfaces ($I_2$), the $I_2-I_1$ value is calculated and used for assessing the hair conditions.

* * * * *